United States Patent
Storck et al.

(10) Patent No.: US 7,151,184 B2
(45) Date of Patent: Dec. 19, 2006

(54) PREPARATION OF PHTHALIC ANHYDRIDE

(75) Inventors: Sebastian Storck, Mannheim (DE);
Frank Rosowski, Mannheim (DE);
Michael Baier, Mannheim (DE);
Andreas Tenten, Overijse (DE);
Hans-Josef Wolf, Maxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 158 days.

(21) Appl. No.: 10/503,983

(22) PCT Filed: Feb. 4, 2003

(86) PCT No.: PCT/EP03/01066

§ 371 (c)(1),
(2), (4) Date: Aug. 10, 2004

(87) PCT Pub. No.: WO03/070680

PCT Pub. Date: Aug. 28, 2003

(65) Prior Publication Data
US 2005/0148782 A1    Jul. 7, 2005

(30) Foreign Application Priority Data
Feb. 19, 2002    (DE)    ............................. 102 06 989

(51) Int. Cl.
*C07D 307/89*    (2006.01)
(52) U.S. Cl. ................................... 549/240
(58) Field of Classification Search ................. 549/240
See application file for complete search history.

(56) References Cited

U.S. PATENT DOCUMENTS

| | | | |
|---|---|---|---|
| 3,565,829 A | 2/1971 | Friedrichsen et al. ....... | 252/464 |
| 3,684,741 A | 8/1972 | Friedrichsen et al. ....... | 252/435 |
| 4,036,783 A | 7/1977 | Blechschmitt et al. | |
| 4,077,984 A | 3/1978 | Blechschmitt et al. | |
| 4,096,094 A | 6/1978 | Blechschmitt et al. | |
| 4,203,906 A | 5/1980 | Takada et al. | |
| 4,282,116 A | 8/1981 | Reuter et al. | |
| 4,284,571 A | 8/1981 | Sato et al. | |
| 4,356,112 A | 10/1982 | Nakanishi et al. | |
| 5,225,574 A | 7/1993 | Aichinger et al. | |
| 5,969,160 A | 10/1999 | Lindstroem | |
| 6,288,273 B1 | 9/2001 | Heidemann et al. | |
| 6,458,970 B1 | 10/2002 | Hefele et al. | |

FOREIGN PATENT DOCUMENTS

| | | |
|---|---|---|
| DE | WO02/16299 | 2/2002 |
| DE | WO03/070680 | 8/2003 |
| EP | 0 163 231 | 12/1985 |
| EP | 0 286 448 | 10/1988 |
| EP | 1 063 222 | 12/2000 |
| WO | WO 98/37965 | 9/1998 |
| WO | WO 98/37967 | 9/1998 |

*Primary Examiner*—Taofiq Solola
(74) *Attorney, Agent, or Firm*—Novak Druce & Quigg, LLP

(57) ABSTRACT

Process for preparing phthalic anhydride by gas-phase oxidation of xylene, naphthalene or mixtures thereof in a shell-and-tube reactor thermostatted by means of a heat transfer medium over three or more different fixed-bed catalysts arranged in zones, wherein the process is carried out so that the maximum temperature in the second catalyst zone in the flow direction is up to 50° C. lower than the maximum temperature in the first catalyst zone and the maximum temperature in the third zone from the gas inlet is from 30 to 100° C. lower than that in the first catalyst zone.

The process of the present invention makes it possible to prepare phthalic anhydride in high yields under industrially relevant conditions.

10 Claims, No Drawings

PREPARATION OF PHTHALIC ANHYDRIDE

The present invention relates to a process for preparing phthalic anhydride by gas-phase oxidation of xylene, naphthalene or mixtures thereof in a shell-and-tube reactor thermostatted by means of a heat transfer medium over three or more different fixed-bed catalysts arranged in zones.

It is known that phthalic anhydride is prepared industrially by catalytic gas-phase oxidation of o-xylene or naphthalene in shell-and-tube reactors. The starting material is a mixture of a gas comprising molecular oxygen, for example air, and the o-xylene and/or naphthalene to be oxidized. The mixture is passed through many tubes which are arranged in a reactor (shell-and-tube reactor) and in which a bed of at least one catalyst is located. To allow the temperature to be regulated, the tubes are surrounded by a heat transfer medium, for example a salt melt. Nevertheless, local temperature maxima (hot spots) in which the temperature is higher than in the remainder of the catalyst bed can occur in the catalyst bed. These hot spots give rise to secondary reactions such as total combustion of the starting material or lead to the formation of undesirable by-products which can be separated from the reaction product only with great difficulty, if at all. In addition, the catalyst can be irreversibly damaged above a certain hot spot temperature.

The hot spot temperatures are usually in the temperature range from 400 to 500° C., in particular in the temperature range from 410 to 460° C. Hot spot temperatures above 500° C. lead to a substantial decrease in the achievable PA yield and in the catalyst operating life. In contrast, hot spot temperatures which are too low lead to a high content of underoxidation products in the phthalic anhydride (in particular phthalide), as a result of which the product quality is significantly impaired. The hot spot temperature depends on the xylene loading of the air stream, on the space velocity of the xylene/air mixture over the catalyst, on the aging state of the catalyst, on the heat transfer characteristics of the fixed-bed reactor (reactor tube, salt bath) and on the salt bath temperature.

Various measures have been employed for decreasing the intensity of these hot spots, and these are described, inter alia, in DE 25 46 268 A, EP 286 448 A, DE 29 48 163 A, EP 163 231 A, DE 41 09 387 A, WO 98/37967 and DE 198 23 362 A. In particular, as described in DE 40 13 051 A, use is now made of catalysts of differing activity arranged in zones in the catalyst bed, with the less active catalyst generally being located nearer the gas inlet and the more active catalyst being located nearer the gas outlet. The process is carried out using a two-stage salt bath, with the salt bath temperature of the first reaction zone in the flow direction of the reaction mixture being kept from 2 to 20° C. higher than the salt bath temperature of the second reaction zone. The catalyst volume of the first reaction zone is from 30 to 75% by volume and that of the second reaction zone is from 25 to 70% by volume. The temperature of the hot spot in the first reaction zone is higher than that in the second reaction zone. The difference between the hot spot temperatures in the modes of operation described in the examples is considerably less than 50° C.

DE 28 30 765 A describes a shell-and-tube reactor which is, inter alia, suitable for the preparation of phthalic anhydride using a catalyst located in two reaction zones. The reaction temperature in the second reaction zone (i.e. follows from the gas inlet) is higher than that in the first reaction zone.

DE 29 48 163 A describes a process for preparing phthalic anhydride using two different catalysts arranged in zones, with the catalyst of the first zone making up from 30 to 70% of the total length of the catalyst bed and the catalyst of the second zone making up from 70 to 30% of the total length of the catalyst bed. This is intended to reduce the temperature of the hot spots. However, it has been found that the yield of phthalic anhydride even at the low o-xylene loadings in the starting gas mixture used in this publication (not more than 85 g/standard m$^3$) leaves something to be desired. A similar disclosure is made in DE 30 45 624 A.

DE 198 23 262 describes a process for preparing phthalic anhydride using at least three coated catalysts arranged in superposed zones, with the catalyst activity increasing from zone to zone from the gas inlet end to the gas outlet end. In this process, the difference in the hot spot temperature from catalyst to catalyst does not exceed 10° C.

EP-A 1 063 222 describes a process for preparing phthalic anhydride which is carried out in one or more fixed-bed reactors. The catalyst beds in the reactors comprise three or more individual catalyst zones arranged in series in the reactor. After passage through the first catalyst zone under the reaction conditions, from 30 to 70% by weight of the o-xylene, naphthalene or mixture of the two in the feed have been reacted. After the second zone, 70% by weight or more have been reacted.

However, the results obtained according to EP-A 1 063 222 are not yet satisfactory, because the heat of reaction and the conversion of the starting materials are not distributed uniformly over the reactor, in particular the catalyst bed, as can be seen from the hot spot profile in FIG. 5 in that publication. Thus, different aging of the catalyst zones occurs and this in turn leads to a decrease in the yield after a prolonged period of operation.

It is an object of the present invention to provide a process for preparing phthalic anhydride which gives high yields of phthalic anhydride even at high o-xylene or naphthalene loads and at high space velocities and in which the heat of reaction is distributed more uniformly over the length of the total catalyst bed, thus contributing to an increased catalyst life.

We have found that this object is achieved if the preparation of phthalic anhydride is carried out over three or more, preferably from three to five, catalysts of differing activity arranged in zones, with the reaction being controlled so that the hot spot temperature in the second catalyst zone from the gas inlet (in the flow direction) is from 0 to 50° C. lower than that in the first catalyst zone and the hot spot temperature in the third catalyst zone from the gas inlet (in the flow direction) is from 30 to 100° C. lower than that in the first catalyst zone.

The present invention accordingly provides a process for preparing phthalic anhydride by gas-phase oxidation of xylene, naphthalene or mixtures thereof in a shell-and-tube reactor thermostatted by means of a heat transfer medium over three or more different fixed-bed catalysts arranged in zones, wherein the process is carried out so that the maximum temperature in the second catalyst zone in the flow direction is up to 50° C. lower than the maximum temperature in the first catalyst zone and the maximum temperature in the third zone from the gas inlet is from 30 to 100° C. lower than that in the first catalyst zone.

The maximum temperature in the second catalyst zone is preferably at least 10–40° C. lower than the maximum temperature in the first catalyst zone. The maximum temperature in the third catalyst zone from the gas inlet (in the flow direction) is preferably from 40 to 80° C. lower than the maximum temperature in the first catalyst zone.

Furthermore, the process is carried out so that the hot spot temperature in the first catalyst zone is less than 470° C. and preferably less than 450° C.

The difference in the hot spot temperatures can be brought about in various ways. For example, it can be achieved by increasing the pressure of the starting gas mixture at the inlet by up to 10% or by lowering the amount of air used for the oxidation by up to 20%. However, the temperature difference is preferably controlled by means of the bed length ratio of the three or more catalyst zones or by means of the temperature of the heat transfer medium (hereinafter, reference will always be made to the preferred heat transfer medium, namely a salt bath), in particular when the three or more catalyst zones are thermostatted by means of different salt bath circuits. The bed length of the first catalyst zone preferably makes up more than 30%, in particular more than 40%, of the length of the total catalyst bed.

If the salt bath temperature is used for control, an increase in the salt bath temperature leads to an increase in the hot spot temperature in the first catalyst zone and to a decrease in the second and each subsequent catalyst zone. In general, a slight increase or decrease, e.g. by 1, 2 or 3° C., is sufficient to set the desired hot spot temperature difference. If the three or more catalyst zones are thermostatted by means of different salt bath circuits, the upper salt bath circuit, i.e. the salt bath circuit which thermostats the first catalyst zone, is preferably operated at a temperature which is from 0.5 to 5° C. higher than that of the lower salt bath circuit. Alternatively, the temperature of the salt bath which thermostats the second catalyst zone is reduced by up to 10° C. and the temperature of the salt bath which thermostats the third catalyst zone is decreased by a further 10° C.

The operating life of the catalyst is generally from about 4 to 5 years. The activity of the catalyst generally decreases a little over time. This can result in the hot spot temperature difference between the first and third catalyst zones dropping below the minimum value of 30° C. It can then be brought back to a value of 30° C. or above by means of the above-described increase in the salt bath temperature. The process is preferably carried out so that the hot spot temperature differences are maintained for at least the first 50%, in particular at least the first 70%, particularly preferably at least the first 90%, of the catalyst operating time and particularly advantageously for essentially the entire catalyst operating time.

The hot spot temperature is determined in a known manner, e.g. by installation of a plurality of thermocouples in the reactor.

Oxidic supported catalysts are suitable as catalysts. To prepare phthalic anhydride by gas-phase oxidation of o-xylene or naphthalene, use is made of spherical, ring-shaped or shell-shaped supports comprising a silicate, silicon carbide, porcelain, aluminum oxide, magnesium oxide, tin dioxide, rutile, aluminum silicate, magnesium silicate (steatite), zirconium silicate or cerium silicate or mixtures thereof. The catalytically active constituents are generally titanium dioxide, in particular in the form of its anatase modification, together with vanadium pentoxide. The catalytically active composition may further comprise small amounts of many other oxidic compounds which act as promoters to influence the activity and selectivity of the catalyst, for example by reducing or increasing its activity. Such promoters are, for example, alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. The alkali metal oxides act, for example, as promoters which reduce the activity and increase the selectivity, while oxidic phosphorus compounds, in particular phosphorus pentoxide, increase the activity of the catalyst but reduce its selectivity. Catalysts which can be used are described, for example, in DE 25 10 994, DE 25 47 624, DE 29 14 683, DE 25 46 267, DE 40 13 051, WO 98/37965 and WO 98/37967. Coated catalysts in which the catalytically active composition is applied in the form of a shell or coating to the support (cf., for example, DE 16 42 938 A, DE 17 69 998 A and WO 98/37967) have been found to be particularly useful.

The less active catalyst is arranged in the fixed bed so that the reaction gas comes into contact firstly with this catalyst and only then with the more active catalyst in the second zone. The reaction gas subsequently comes into contact with the even more active catalyst zones. The catalysts of differing activity can be thermostatted to the same temperature or to different temperatures. In general, a catalyst doped with alkaline metal oxides is used in the first catalyst zone nearest the gas inlet and a catalyst doped with a smaller amount of alkali metal oxides and/or phosphorus compounds and/or further promoters is used in the second reaction zone. A catalyst doped with still smaller amounts of alkali metal oxides or phosphorus compounds and/or further promoters is used in the third catalyst zone.

Particular preference is given to catalysts having the following compositions:

for the first zone: from 3 to 5% by weight of vanadium pentoxide from 0.1 to 1% by weight of an alkali metal oxide, e.g. cesium oxide from 94 to 96.9% by weight of titanium dioxide for the second zone: from 4 to 7% by weight of vanadium pentoxide from 0 to 0.5% by weight of an alkali metal oxide, e.g. cesium oxide from 0.05 to 0.4% by weight of phosphorus pentoxide (calculated as P) balance to 100% by weight: titanium dioxide for the third zone: from 6 to 9% by weight of vanadium pentoxide from 0 to 0.3% by weight of an alkali metal oxide, e.g. cesium oxide from 0.05 to 0.4% by weight of phosphorus pentoxide (calculated as P) if desired, from 1 to 5% by weight of a further promoter, in particular $Sb_2O_3$ from 85.3 to 93.95% by weight of titanium dioxide The reaction is generally carried out so that the major part of the o-xylene and/or naphthalene present in the reaction gas is reacted in the first reaction zone.

For the reaction, the catalysts are introduced in layers (zones) into the tubes of a shell-and-tube reactor. The reaction gas is passed over the catalyst bed prepared in this way at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, and at a space velocity of generally from 750 to 5000 $h^{-1}$, preferably from 2000 to 5000 $h^{-1}$. The reaction gas fed into the catalyst bed (starting gas mixture) is generally produced by mixing a gas which comprises molecular oxygen and may further comprise, in addition to oxygen, appropriate reaction moderators and/or diluents such as steam, carbon dioxide and/or nitrogen with the o-xylene or naphthalene to be oxidized. The reaction gas generally contains from 1 to 100 mol %, preferably from 2 to 50 mol % and particularly preferably from 10 to 30 mol %, of oxygen. In general, the reaction gas is loaded with from 5 to 140 g/standard m³ of gas, preferably from 60 to 120 g/standard m³ and particularly preferably from 80 to 120 g/standard m³, of o-xylene and/or naphthalene.

If desired, a downstream finishing reactor as described, for example, in DE 198 07 018 or DE 20 05 969 A may additionally be provided for the preparation of phthalic anhydride. The catalyst used here is preferably a catalyst which is even more active than the catalyst of the third zone. In particular, this catalyst has the following composition:

from 6 to 9% by weight of vanadium pentoxide
from 1 to 5% by weight of an activity-increasing promoter, in particular $Sb_2O_3$
from 0.1 to 0.5% by weight of phosphorus pentoxide (calculated as P)
from 85.5 to 92.9% by weight of titanium dioxide.

The process of the present invention has the advantage that phthalic anhydride can be prepared in high yield and with low concentrations of by-products, in particular phthalide, even at high o-xylene and/or naphthalene loadings and at high space velocities. Under the conditions of the process of the present invention, the phthalide concentration is no more than 0.1% by weight, based on PA. The advantages of the process of the present invention are particularly evident when the activity of the catalyst system used decreases as a result of aging. Even after a long running time, there is only an insignificant increase in the hot spot temperature in the second catalyst zone.

The temperature control method provided according to the present invention can also be used in preparation of other products by catalytic gas-phase oxidation, e.g. acrylic acid (from propene), maleic anhydride (from benzene, butene or butadiene), pyromellitic anhydride (from durene), benzoic acid (from toluene), isophthalic acid (from m-xylene), terephthalic acid (from p-xylene), acrolein (from propene), methacrylic acid (from isobutene), naphthoquinone (from naphthalene), anthraquinone (from anthracene), acrylonitrile (from propene) and methacrylonitrile (from isobutene).

The following examples illustrate the invention without restricting its scope.

EXAMPLES

1) Production of the Catalysts I–IV

Catalyst I:

50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 20 m²/g, 2.19 kg of vanadyl oxalate, 0.176 kg of cesium sulfate, 44.1 kg of water and 9.14 kg of formamide until the weight of the applied layer was 10.5% of the total weight of the finished catalyst (after calcination at 450° C.).

The catalytically active composition applied in this way, i.e. the catalyst shell, comprised 4.0% by weight of vanadium (calculated as $V_2O_5$), 0.4% by weight of cesium (calculated as Cs) and 95.6% by weight of titanium dioxide.

Catalyst II:

The procedure for the preparation of catalyst I was repeated using 0.155 kg of cesium sulfate, which led to a cesium content of 0.35% by weight (calculated as Cs).

Catalyst III 50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 20 m²/g, 4.11 kg of vanadyl oxalate, 1.03 kg of antimony trioxide, 0.179 kg of ammonium dihydrogen phosphate, 0.045 kg of cesium sulfate, 44.1 kg of water and 9.14 kg of formamide until the weight of the applied layer was 10.5% of the total weight of the finished catalyst (after calcination at 450° C.).

The catalytically active composition applied in this way, i.e. the catalyst shell, comprised 0.15% by weight of phosphorus (calculated as P), 7.5% by weight of vanadium (calculated as $V_2O_5$), 3.2% by weight of antimony (calculated as $Sb_2O_3$), 0.1% by weight of cesium (calculated as Cs) and 89.05% by weight of titanium dioxide.

Catalyst IV 50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 11 m²/g, 3.84 kg of vanadyl oxalate, 0.80 kg of antimony trioxide, 0.239 kg of ammonium dihydrogen phosphate, 44.1 kg of water and 9.14 kg of formamide until the weight of the applied layer was 12.5% of the total weight of the finished catalyst (after calcination at 450° C.).

The catalytically active composition applied in this way, i.e. the catalyst shell, comprised 0.2% by weight of phosphorus (calculated as P), 7.0% by weight of vanadium (calculated as $V_2O_5$), 2.5% by weight of antimony (calculated as $Sb_2O_3$) and 90.3% by weight of titanium dioxide.

2) Oxidation of o-xylene

2a) Preparation of PA—According to the Present Invention and Comparison (Setting of the Hot Spot Temperature Difference by Varying the Bed Lengths)

In a 10 l tube reactor (99 normal tubes and 2 thermocouple-contained tubes), each of the 3.60 m long iron tubes having an internal diameter of 25 mm (thermocouple-containing tubes 29 mm with thermocouple sheath 10 mm internal diameter and 30 installed thermocouples (every 10 cm)) was charged from the bottom upward with catalyst III (comparison: 1.30 m; according to the present invention: 0.70 m), catalyst II (according to the present invention: 0.80 m) and subsequently catalyst I (1.70 m (comparison); according to the present invention: 1.50 m). It was ensured by means of pressure matching that the pressure at the inlet of each tube was the same. If necessary, a little catalyst I was added or sucked out from the 99 normal tubes; in the case of the two thermocouple-containing tubes, pressure matching was achieved by addition of inert material in the form of steatite spheres or quartz spheres. The iron tubes were surrounded by a salt melt which was located in two separate salt baths to regulate the temperature. The lower salt bath surrounded the tubes from the bottom tube plate to a height of 1.30 m, and the upper salt bath surrounded the tubes from the height of 1.30 m to the upper tube plate. Air laden with 100 g of 98.5% purity by eight o-xylene per standard m³ of air (after a running-up time of about two months) was passed through the tubes from the top downward at a flow rate of 4.0 standard m³/h per tube. After leaving the main reactor, the crude product gas stream was cooled to 280–290° C. and passed through an adiabatic finishing reactor (internal diameter: 0.45 m, height: 0.99 m) charged with 100 kg of catalyst IV.

The data listed in the following table were obtained in the experiment (running day=day of operation from the first start-up of the catalyst; SBT top=salt bath temperature of the salt bath nearest the reactor inlet; SBT bottom=salt bath temperature of the salt bath nearest the reactor outlet; HS top=hot spot temperature of the catalyst nearest the reactor inlet; HS bottom=hot spot temperature of the catalyst nearest the reactor outlet; PHD content and xylene content=phthalide content and xylene content, respectively, of the crude product gas downstream of the finishing reactor, based on phthalic anhydride; PA yield=yield of PA in % by weight based on 100%-pure xylene derived from the analysis of the crude product gas downstream of the finishing reactor).

2b) Preparation of PA—According to the Present Invention (Temperature Variation and Temperature Structuring)

After the catalyst combination operated in 2a) as comparative experiment had been run for 250 days, a temperature difference of >40° C. was set by means of temperature structuring (SBT bottom reduced or SBT top increased) or temperature variation (SBT bottom and top increased). All other experimental conditions remained unchanged from those in experiment 2a).

The data listed in the following table were then obtained (running day=day of operation from the first start-up of the catalyst; SBT top=salt bath temperature of the salt bath nearest the reactor inlet; SBT bottom=salt bath temperature of the salt bath nearest the reactor outlet; HS top=hot spot temperature of the catalyst nearest the reactor inlet; HS bottom=hot spot temperature of the catalyst nearest the reactor outlet; PHD content and xylene content=phthalide content and xylene content, respectively, of the crude product gas downstream of the finishing reactor, based on phthalic anhydride; PA yield=yield of PA in % by weight based on 100%-pure xylene derived from the analysis of the crude product gas downstream of the finishing reactor).

| Bed | Running day [d] | SBT top SBT bottom [° C.] | HS top [° C.] | HS middle [° C.] | HS bottom [° C.] | Δ T top-middle [° C.] | Δ T top-bottom [° C.] | PA yield [%] |
|---|---|---|---|---|---|---|---|---|
| Comparison 170/130 | 100 | 348/348 | 434 | — | 366 | — | 68 | 113.1 |
|  | 150 | 348/348 | 434 |  | 375 |  | 57 | 112.9 |
|  | 200 | 348/348 | 421 |  | 390 |  | 31 | 112.0 |
|  | 250 | 348/348 | 419 |  | 394 |  | 25 | 111.3 |
| According to the present invention 150/80/70 | 100 | 348/348 | 430 | 400 | 360 | 30 | 70 | 113.3 |
|  | 150 | 348/348 | 431 | 402 | 359 | 29 | 71 | 113.1 |
|  | 200 | 348/348 | 425 | 413 | 361 | 12 | 64 | 112.9 |
|  | 250 | 348/348 | 421 | 411 | 362 | 10 | 59 | 112.7 |

| Bed 170/130 | Running day [d] | SBT top/ SBT bottom [° C.] | HS top [° C.] | HS bottom [° C.] | Temperature difference [° C.] | PA yield [m/m %] |
|---|---|---|---|---|---|---|
| Comparison without temperature structuring | 250 | 348/348 | 419 | 394 | 25 | 111.3 |
| according to the present invention with temperature increase | 252 | 349/349 | 428 | 387 | 41 | 112.3 |
|  | 254 | 350/350 | 437 | 381 | 56 | 112.5 |
| according to the present invention with temperature structuring | 256 | 349/348 | 429 | 385 | 44 | 112.5 |
|  | 258 | 350/348 | 438 | 379 | 58 | 112.8 |
|  | 260 | 348/343 | 419 | 381 | 38 | 112.0 |
|  | 262 | 348/338 | 418 | 370 | 48 | 112.9 |
|  | 264 | 348/335 | 419 | 365 | 54 | 113.1 |

The results reported under 2a) show that the PA yield correlates with the hot spot temperature difference, i.e. PA is obtained in high yield under industrially relevant operating conditions when the temperature difference between the first and second catalyst zones is in the range from 0 to 50° C. and that between the first and third catalyst zones is in the range from 30 to 100° C.

The results reported under 2b) show that when the hot spot temperature difference is too low, the hot spot temperature difference in the dual-structure bed can be increased again either by simultaneously increasing the salt bath temperature top and bottom to a small extent or by reducing the temperature of the lower salt bath while maintaining the same temperature in the upper salt bath.

We claim:

1. A process for preparing phthalic anhydride by gas-phase oxidation of xylene, naphthalene or mixtures thereof in a shell-and-tube reactor thermostated by means of a heat transfer medium over three or more different supported ring-shaped fixed-bed catalysts arranged in zones, wherein the process is carried out so that the maximum temperature in the second catalyst zone in the flow direction is from 10 to 40° C. lower than the maximum temperature in the first catalyst zone, the maximum temperature in the third zone from the gas inlet is from 30 to 100° C. lower than that in the first catalyst zone, and the maximum temperature in the first catalyst zone is less than 470° C.

2. A process as claimed in claim 1, wherein the maximum temperature in the third catalyst zone is from 40 to 80° C. lower than in the first catalyst zone.

3. A process as claimed in claim 1, wherein the temperature difference between the maximum temperature in the first, second and third catalyst zones is controlled by means of the bed length ratio of the catalyst zones.

4. A process as claimed in claim 3, wherein the bed length of the first catalyst zone is more than 30% of the length of the total catalyst bed.

5. A process as claimed in claim 3, wherein the bed length of the first catalyst zone is more than 40% of the length of the total catalyst bed.

6. A process as claimed in claim 1, wherein the temperature difference between the maximum temperature in the first catalyst zone and in the second catalyst zone is controlled via the temperature of the heat transfer medium.

7. A process as claimed in claim 1, wherein the maximum temperature in the first catalyst zone is less than 450° C.

8. A process as claimed in claim 1, wherein a gas phase having a loading of from 80 to 140 g of o-xylene and/or naphthalene per standard $m^3$ of gas phase used.

9. A process as claimed in claim 1, wherein the temperature of the heat transfer medium is $\leq 360°$ C.

10. A process as claimed in claim 1, wherein the space velocity of the gas mixture is $\geq 2000$ $h^{-1}$.

* * * * *